(12) United States Patent
Itagaki

(10) Patent No.: US 7,292,338 B2
(45) Date of Patent: Nov. 6, 2007

(54) PARTICLE DETECTION APPARATUS AND PARTICLE DETECTION METHOD USED THEREFOR

(75) Inventor: Nobutaka Itagaki, Tokyo (JP)

(73) Assignee: Avago Technologies ECBU IP (Singapore) Pte Ltd, Singapore (AG)

( * ) Notice: Subject to any disclaimer, the term of this patent is extended or adjusted under 35 U.S.C. 154(b) by 0 days.

(21) Appl. No.: 11/509,168

(22) Filed: Aug. 24, 2006

(65) Prior Publication Data
US 2007/0097372 A1    May 3, 2007

(30) Foreign Application Priority Data
Aug. 24, 2005 (JP) .............................. 2005-242605

(51) Int. Cl.
*G01N 21/00*    (2006.01)
(52) U.S. Cl. .................................... 356/337; 382/107
(58) Field of Classification Search ............... 356/337, 356/338, 339, 342, 438
See application file for complete search history.

(56) References Cited

U.S. PATENT DOCUMENTS 5,721,433 A * 2/1998 Kosaka ...................... 250/573
5,905,568 A * 5/1999 McDowell et al. ............ 356/28
5,923,260 A * 7/1999 Endo et al. .................. 340/630
6,603,535 B1 * 8/2003 McDowell .................... 356/28

FOREIGN PATENT DOCUMENTS

WO    WO 9940410 A1 *    8/1999

* cited by examiner

Primary Examiner—Roy M. Punnoose (57) ABSTRACT

A particle detection apparatus and a detection method used therefor, which can detect dust, pollen and smoke particles at a high sensitivity with a sufficiently simple configuration. A particle detection apparatus has a light source and a detection device for detecting light from the light source, and detects particles floating in the air at a position through which the light passes. The apparatus further has an airflow generation/control device capable of controlling an airflow of the air present in the light passing position so as to keep the airflow constant or nearly zero, and an image sensor is used as a photodetector of the detection device. Predefined particles are identified from image information including a moving speed, a size and a shape of a moving object detected by the image sensor.

10 Claims, 5 Drawing Sheets

PARTICLE DETECTION APPARATUS AND PARTICLE DETECTION METHOD USED THEREFOR

BACKGROUND OF THE INVENTION

1. Field of the Invention

[Technical Field]

The present invention relates to a particle detection apparatus for detecting fine particles floating in the air, such as dust, pollen and smoke, and a particle detection method used therefor.

2. Description of Related Art

[Background Art]

In recent years, as the number of patients suffering from allergy such as hey fever increases, there is a growing concern on indoor conditions. Therefore, in relation to products such as an air cleaner and an air conditioner, there is a demand for detecting, at a high sensitivity, fine particles such as dust, pollen and cigarette smoke, which may present in an environment where those products are used.

In many buildings, air conditioning facilities are equipped to keep indoor conditions at a predetermined level or above. In order to maintain predetermined indoor conditions, regulations are imposed upon those facilities by laws and ordinances so that an amount of floating dust be kept at a predetermined level or below. In recent years, on the other hand, it is desired to efficiently operate air conditioning facilities from a viewpoint of energy saving. Accordingly, there is a strong demand for means for measuring an amount of floating dust more accurately.

Conventionally, there are known various sensor devices and detection methods for detecting fine particles such as dust, pollen and smoke floating in a room.

As one example, an apparatus having an intake function is known, according to which a gas to be measured is taken from the outside, light is illuminated from an internal LED to the gas to be measured, and light scattered by particles floating in the gas is detected for determining existence of the particles (Patent Document 1).

There is also known an apparatus for detecting particles from changes in polarization state of transmitted light, rather than measurements of scattered light (Patent Document 2). In this apparatus, light to be illuminated is pulsed to separately detect dust and smoke. Since smoke is composed of very fine particles (particle diameter: 0.01 micrometer to several micrometers), it stays in the air for a relatively long period of time. On the other hand, dust or pollen is larger in particle size and heavier. Therefore, they drift through the air, but have a higher falling speed. Accordingly, when a light pulse is applied, a sensor output changes gradually when smoke enters into the apparatus. However, when dust enters into the apparatus, the sensor output changes rapidly compared to the case where smoke enters, and it is possible to distinguish dust from smoke. In both cases, dust and smoke are identified from information on temporal changes.

Further, a sensor apparatus for detecting pollen, wherein a laser is used to distinguish pollen from other fine particles is known (Patent Document 3). In that apparatus, a laser and two photodetectors are used. First, laser light is illuminated to a gas to be measured, and two scattered light components, i.e., vertical and horizontal polarized light components are detected regarding the illuminated laser light, and an output therefrom enables identification between pollen and other particles. Based on differences in polarization states of the scattered light, pollen is distinguished from other fine particles.

[Patent Document 1] Japanese Patent Laid-Open Publication No. 2000-356,583

[Patent Document 2] Japanese Patent Laid-Open Publication No. 2001-83,079

[Patent Document 3] Japanese Patent Laid-Open Publication No. 2004-125,602

SUMMARY OF THE INVENTION

In conventional apparatus, particles having a specific size can be detected at a certain level of sensitivity, and some of them have been put into practical use. However, their performances are not always satisfactory, and further improvements are required.

For example, an existing fine particle sensor employs a photo diode or a phototransistor for detection. Utilizing an effect that light is scattered or shielded by fine particles such as dust, pollen and smoke particles, the existence thereof is detected. In such sensor, a sensor output is a value that is solely dependent upon the size and reflectivity (for scattering) of fine particles. Therefore, it is difficult to distinguish dust from pollen when the fine particles are 20 to 50 micrometers in size. The method utilizing polarized light mentioned above may be used, but it also may not be completely satisfactory.

Therefore, an object of the present invention is to provide a particle detection apparatus and a detection method used therefor, which can detect dust, pollen, and smoke particles at a high sensitivity while having a sufficiently simple configuration compared to conventional systems and methods. A further object of the present invention is to provide an apparatus and a method, which can individually output floating amounts of dust, pollen and smoke particles by analyzing the detected data.

A particle detection apparatus of the present invention particularly employs an image sensor as means for detecting light. The image sensor is typically a CMOS image sensor, but a CCD image sensor and the like may also be used. The present invention uses an image sensor having light detection elements arranged two- or one-dimensionally, thereby enabling to observe fine particles at a high sensitivity.

In accordance with the present invention, particles are efficiently identified by utilizing properties of the particles. The properties of the particles are as indicated below:

(a) smoke particles: having a size of one micrometer or less, and evenly distributed in a gas;

(b) pollen: having a size of 20 micrometers to 50 micrometers, heavy, and sporadically appears; and (c) dust: having a size of 100 micrometers or less; light; and sporadically appears.

Then, the apparatus of the present invention has means capable of generating an airflow in the air containing particles to be measured. The airflow is generated in a direction against the gravity (e.g. upwardly), or in a direction along the gravity (e.g. downwardly).

Particle identification is carried out by following the algorithm described below.

(A) Identifying Smoke Particles

Smoke particles are small, and they are evenly diffused spatially when the smoke is taken into the apparatus. Therefore, when a measurement is made with the image sensor, a change in image information occurs over the entire area to be imaged when the air is introduced. Further, according to an output from the image sensor, it is detected that a spatial standard deviation of smoke is very small compared to those of dust and pollen. In this process, fine particles that are not determined to be smoke are determined to be dust or pollen.

(B) Identifying Between Dust and Pollen (B-1) An output from the image sensor is binarized with a predetermined threshold, and the size of particles that are scattering or shielding is determined. When the determined size is 20 micrometers or less or 50 micrometers or more, the particles are considered to be dust.

(B-2) When the size of fine particles is determined to be between 20 micrometers and 50 micrometers, a moving speed of the floating particles is calculated. When the moving speed is at or greater than a predetermined level, the particles are determined to be dust, and otherwise the particles are determined to be pollen. When the airflow is not a rising airflow and fine particles flow from top to down, particles are determined to be pollen when they have a fast moving speed and dust when they have a slow moving speed. The moving speed of floating particles is calculated by mapping (correlating) outputs obtained from the image sensor on a time axis.

The present invention provides a particle detection apparatus which comprises a light source and a photodetector for detecting light from the light source to detect particles floating in the air at a position through which the light passes. The apparatus further comprises an airflow generation/control device capable of controlling an airflow of the air at the position through which the light passes, so as to keep the airflow at a constant rate or nearly zero, and an image sensor is used as the photodetector so as to identify predefined particles from image information including the moving speed, size and shape of a moving object detected by the image sensor.

The light source and the image sensor are disposed so that light from the light source can be directly received by the image sensor, and the airflow generation/control device is configured so that the airflow generated thereby intersects with the light. Alternatively, the light source and the image sensor are disposed to oppose across or on the same side of the airflow generated by the airflow generation/control device in tilted directions, so that the image sensor receives scattered light or reflected light produced within the airflow from the light of the light source. The weight of a moving object is determined from the moving speed of the moving object when the airflow is made constant. The light source is typically composed of a semiconductor light-emitting element.

Further, the present invention provides a particle detection method comprising the steps of generating an airflow in the air in which particles are floating, illuminating light to a position at which the airflow is generated, detecting the light passing through the airflow or the light scattered by the particles in the airflow, and identifying predefined particles from image information including the moving speed, size and shape of a moving object specified by the detected light.

Furthermore, the method may also comprise a step of determining the weight of the moving object from the moving speed of the moving object when the airflow is kept constant. The light to be illuminated is light having a relatively high directional characteristic, which is typically provided by a semiconductor light-emitting element. In addition, if the size, concentration and the like of particles to be measured fall under predetermined conditions, particle diffusion in a natural state may be utilized without vigorously generating airflow.

According to the present invention, a particle detection apparatus and a method therefor, which have a relatively simple configuration but can detect dust, pollen and smoke particles at a high sensitivity are obtained. In particular, according to the apparatus and method of the present invention, individual amounts of dust, pollen and smoke particles floating in the air can be obtained as outputs, and such outputs can be effectively utilized as parameters for environmental analysis or for controlling equipment such as air conditioning facilities.

DETAILED DESCRIPTION OF THE PREFERRED EMBODIMENTS

Hereinafter, a particle detection apparatus and a particle detection method, the best mode for carrying out the present invention, will be described in detail with reference to the accompanying drawing figures.

Figure 1:
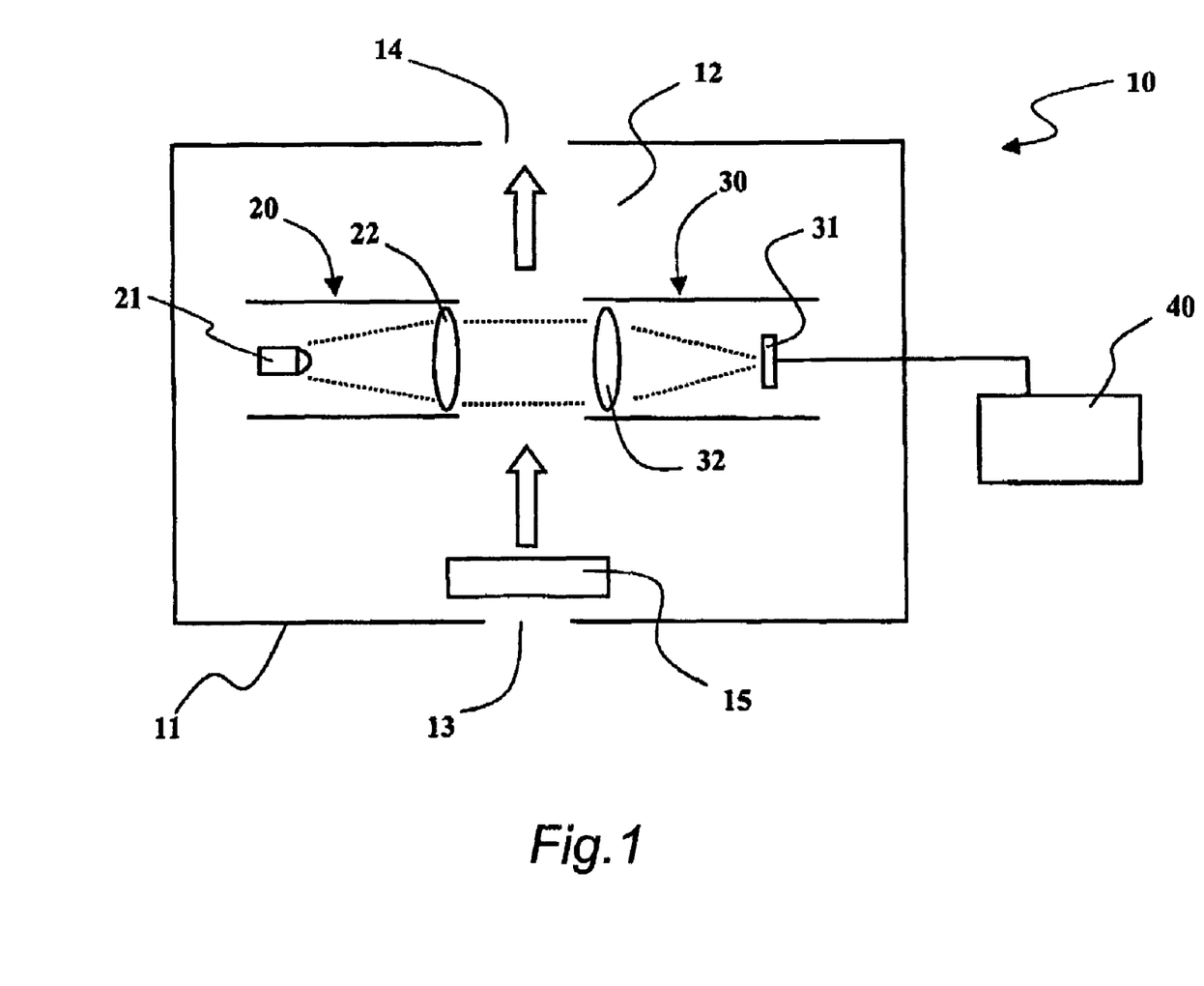
FIG. 1 is a schematic view showing a configuration of a particle detection apparatus of a first embodiment according to the present invention.

FIG. 1 is a schematic view showing a configuration of a particle detector according to a first embodiment of the present invention. An apparatus 10 has a chamber 12 surrounded by a wall 11, and the chamber 12 has an inlet 13 for taking air from the outside and an outlet 14 for discharging air. In order to take air and generate airflow at a particle detection position as later described, an airflow generating/controlling device 15 is provided on the inner side of the inlet 13. Even when the airflow generating/controlling device 15 is not turned on, air can flow between the inlet 13 and outlet 14.

As the airflow generating/controlling device 15, a small fan is typically used. However, in order to generate airflow in a rising direction opposite to the gravity, an air heating device such as a heater may be used. Air entered from the inlet 13 into the chamber 12 passes through the inside of the chamber 12 and is guided to the outlet 14. Though not shown, airflow guide means having, for example, a cylindrical shape may be provided between the inlet 13 and the outlet 14. Further, a filter may be installed at a prior stage to the airflow generating/controlling device 15 to prevent the entry of particles having a size greater than target fine particles.

The apparatus 10 also includes means for detecting a particle. That means includes a light source 20 and a detection device 30. In this embodiment, the light source 20 and the detection device 30 are arranged horizontally in an opposing manner. This allows the detection device 30 to directly receive light from the light source 20, and the light source 20 and the detection device 30 are configured to pass the airflow generated by the airflow generating/controlling device 15 between them.

The light source 20 is composed of a light-emitting element 21 and an optical system 22 including a lens. The light-emitting element 21 may be typically composed of a semiconductor light-emitting element such as a laser diode or a light-emitting diode capable of emitting coherent light. If the degree of sensitivity is not pursued, other light-emitting element may be used. However, a light-emitting element capable of emitting light with a certain degree of directional characteristics is desired from the viewpoint of device design.

On the other hand, the detection device 30 is composed of a photodetector 31 and an optical system 32 including a lens. As the photodetector 31, an image sensor such as a CMOS image sensor or a CCD image sensor may be used. The photodetector 31 is configured so as to output a detection signal to an external analyzer 40.

Light emitted from the light emitting-element 21 passes through the optical system 22, and is illuminated to a gas to be measured. In one embodiment, light emitted from the light emitting-element 21 is substantially collimated by the optical system 22. The light passing through the gas in the measurement area is collected by the optical system 32 in the detection device 30, and detected as an image by an image sensor 31. The image sensor 31 outputs a signal of the image to the analyzer 40.

Optical dimensions of the lens in the optical system 22, such as a focal length, can be determined based on a radiation angle of light from the light-emitting element 21 and a diameter of fine particles to be measured. Specifically, it is necessary to select a focal length of the lens so that a light flux has a diameter several times larger than the size of the fine particles to be measured. For example, in measuring fine particles having a size of approximately 100 micrometers, it is necessary to illuminate light in such a way that the light has a diameter of not less than several hundred micrometers, so as to keep the sensitivity of the entire system. However, if light is illuminated to a large area, the power of transmitted light to be detected decreases, resulting in a degraded signal/noise ratio. Therefore, optimization may be necessary.

Figure 2:
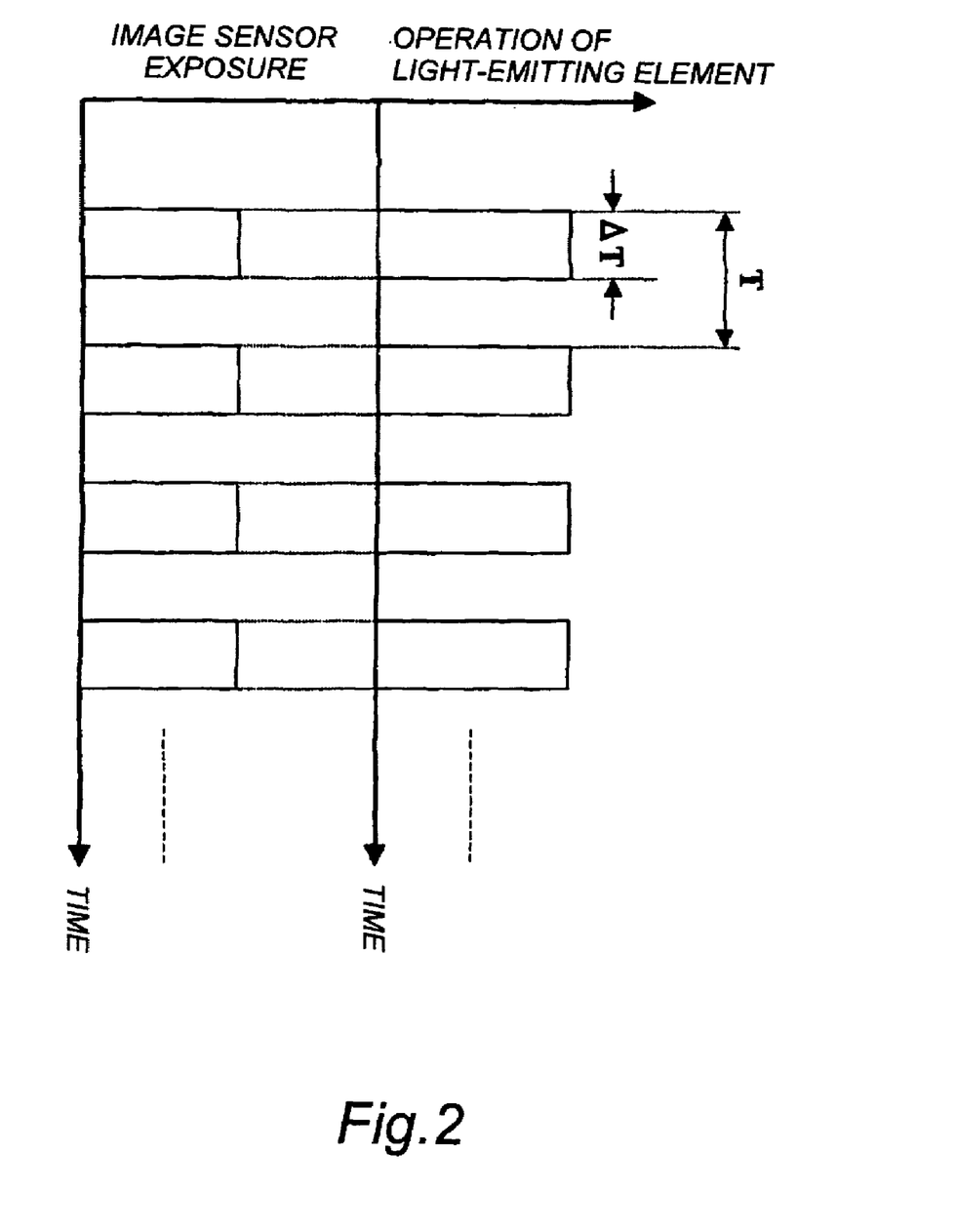
FIG. 2 is a time chart showing the timing of the operation of the light emitting-element and the exposure of the image sensor.

FIG. 2 is a time chart showing the timing of the operation of the light emitting-element and the exposure of the image sensor. The light emitting-element 21 such as a laser diode is made to generate light pulses rather than continuous light (CW) for the purpose of reducing power consumption. The cycle (T) of a light pulse and a time period (ΔT) for illumination are properly selected from the moving speed of fine particles to be measured. If the cycle T is too long, problems may arise that, for example, fine particles themselves may not be detected or a captured image becomes blurred. If the cycle T is too short, the light application time ΔT is also short and thus there is a drawback that the signal/noise ratio is degraded.

In FIG. 1, the exposure time of the image sensor 31 is the same as that of the light emitting-element 21. This period is optimized by taking into consideration the signal/noise ratio of the entire system. The number of pixels of the image sensor mainly depends upon the size of fine particles to be measured. If the size of fine particles to be measured is from 1 micrometer to 100 micrometers, the number of pixels may be approximately 10,000.

Hereafter, an algorithm for detecting smoke particles, dust and pollen will be described. This method is not limited to the present embodiment, any may be applied to apparatus according to second and third embodiments described later.

Here, an output taken by the image sensor along x-axis (i-th) and y-axis (j-th) is indicated as $V(i,j)$. Depending on the configuration of a focal length of a lens, there may be a difference in an output of the image sensor per pixel. Therefore, calibration is carried out at the beginning to adjust all of the pixels so that offset and sensitivity fall within a certain range. This adjustment may be carried out by hardware means or software means. In the following description, $V(i,j)$ is an output value after the adjustment is carried out.

First, a state without the presence of obstacles, such as smoke particles, dust and pollen, is considered. In this case, transmitted light is detected directly by the image sensor without scattering, and thus its output $V\_non(i,j)$ has a very small variance $\sigma\_non$ for the entire pixels.

When any of fine particles such as smoke particles, dust or pollen is entered, light is scattered thereby, resulting in a reduction in an amount of transmitted light. This enables to detect the fine particles. A predetermined value $V\_noise$ is set by taking into accounts the stability of LD inside the detection apparatus, shot noises which may occur in the image sensor, noises in amplifier circuitry, and thermal noises. If this value is exceeded, it is determined that a signal is supplied. While the fine particles may be introduced by generating an airflow, natural diffusion or natural introduction of particles may be utilized without generating the airflow.

When it is determined that a signal is supplied, smoke particles, dust and pollen are distinguished in accordance with the following procedure.

1. When it is determined that a signal is supplied to all of the pixels, that is determined to be attributable to smoke particles.

In other words, when $$V(i,j)<V\_non-V\_detect\_1$$

is valid for all of the pixels, smoke particles are identified. Here, $V\_detect\_1$ is a constant threshold larger than $V\_noise$. Even if very large particles are introduced, the signal is detected in all of the pixels. However, as stated previously, in this case, such particles are removed in advance by a filter. Further, a concentration of the smoke is identified depending on an intensity of the signal.

Figure 3A:
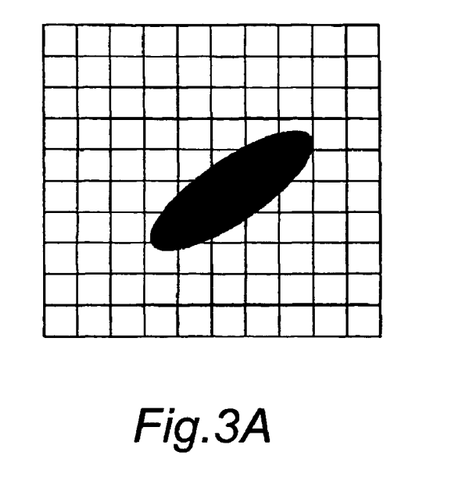
FIGS. 3A to 3B are views showing schematized image information of a binarized particle image.
Figure 3B:
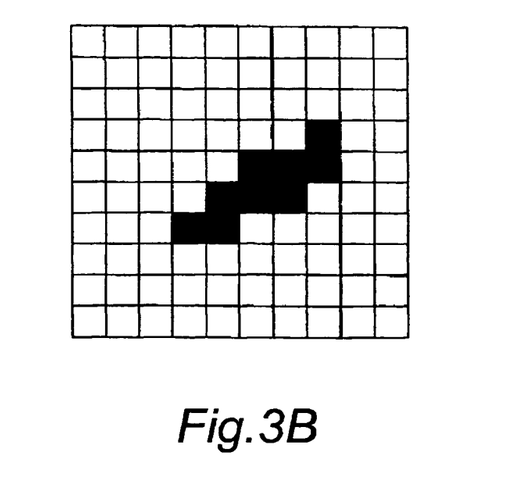

2. When part of pixels have responded, dust or pollen is identified. Binarization is carried out to identify a portion shielded by fine particles. FIG. 3 is a view schematically showing such binarization. For example, if a dust has a size and shape as shown in (a), that is identified by binarization as an image as shown in (b). $V\_detect\_2$ is used as a parameter for performing the binarization, and pixels that output a signal exceeding this threshold $V\_detect\_2$ are counted. The count number is proportional to a light-shielding cross-sectional area by the fine particles, with respect to the incident light. On the basis of the counted pixel number, fine particles of 20 micrometers or less or 50 micrometers or more are identified as dust.

3. When the result of the above size measurement of the fine particles indicates that the particles are determined to have a size from 20 micrometer to 50 micrometer, it is possible that the particles are pollen. Therefore, in such a case, determination by a further method is necessary. In general, since dust is lighter than pollen, dust has a higher moving speed in an airflow than pollen. Therefore, the moving speed of floating particles is calculated. When the moving speed of the particles is at a predetermined level or higher, those particles are determined to be dust, and otherwise they are determined to be pollen. When the airflow is not rising and the fine particles flow from top to down, the particles having a higher moving speed is considered pollen and slow particles are considered dust.

Figure 4A:
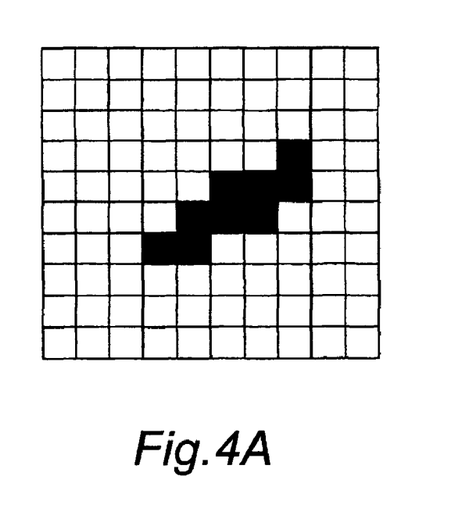
FIGS. 4A to 4B are views showing temporal changes of a binarized image signal.
Figure 4B:
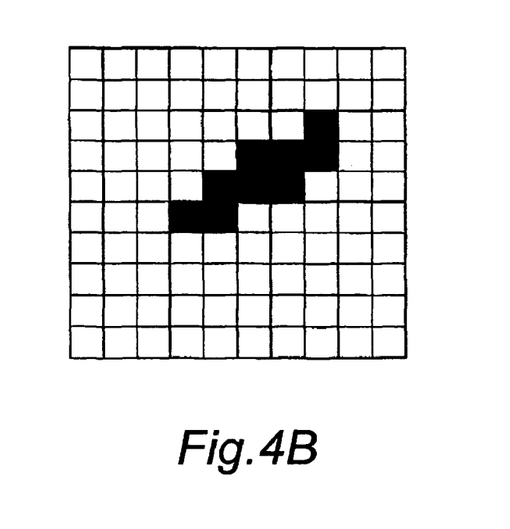

The speed value is obtained by taking two images at successive units of time, and calculating from a moving distance between the images and a frame time. FIGS. 4A and 4B show temporal a change in a binarized image signal. In this example, it is recognized that a particle is moving upwardly. In order to recognize movement of particles from image information, a correlation value conventionally used in related technology can be utilized. As a result of determining the moving speed, when it is not lower than or not higher than a predetermined speed, the particles can be identified as dust or pollen, respectively.

In this description, detection of fine particles such as dust and pollen has been mainly described. However, by improving the analytical algorithm of the present apparatus, it is possible to produce a histogram of passing particles over a certain period in terms of size or weight of fine particles contained in an introduced gas. From this result, it is possible to analyze what types of fine particles exist in a room or in the open air.

Figure 5A:
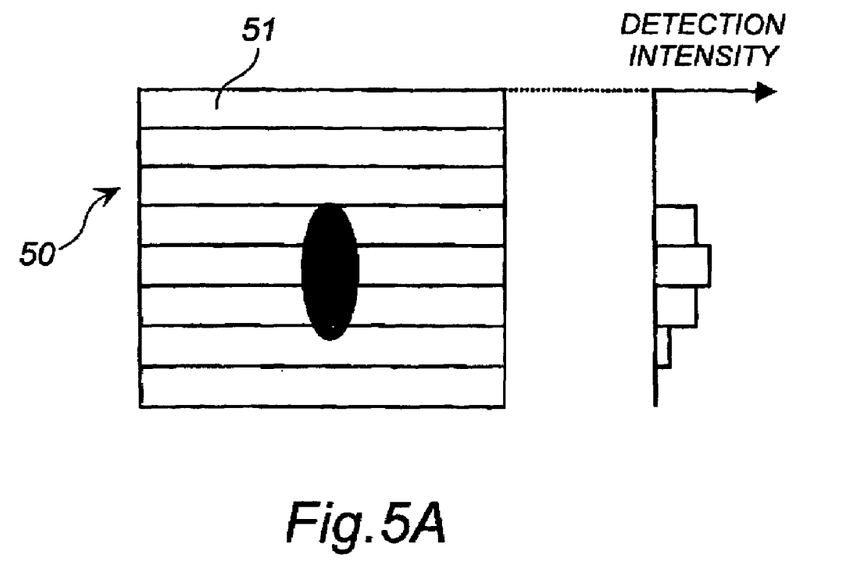
FIGS. 5A to 5B are views showing a modified embodiment of a photodetector, which indicate particle detection at different times for each view. Each view shows a positional relation between the photodetector and the particle at left side and output values at right side.
Figure 5B:
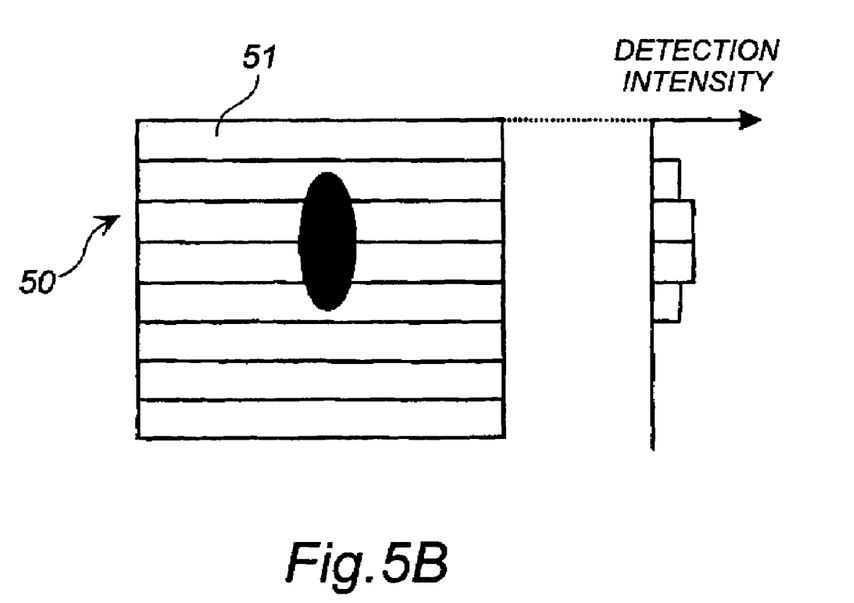

FIG. 5 is a view describing a modified embodiment of the photodetector. In the aforementioned embodiment, the image sensor as a photodetector is provided with detection elements in the form of a matrix of approximately 100×100. However, a photodetector is not necessarily provided with a matrix of detection elements, and a photodetector having detection elements 51 disposed in a striped form may be used. That is, in this apparatus, when an airflow is generated, the moving direction of fine particles is considered to run along a direction of the airflow. Therefore, detection of particles as in the foregoing embodiment is possible, by utilizing a photodetector 50 having a striped configuration wherein elongated detection elements 51 are extended in a direction perpendicular to the moving direction of the fine particles.

FIGS. 5A and 5B show particle detection at different times when the photodetector 50 is used. In each figure, a positional relation between the photodetector and a particle is shown on the left and output values are shown on the right. FIG. 5A shows an initial state and FIG. 5B show a state after a predetermined time period after the state of FIG. 5A. Each of the detection elements 51 constituting a stripe can output a signal which is substantially proportional to the area of an image. Therefore, by establishing and comparing the output values, the position of a particle at that time and a particle moving speed may be determined. For example, when data obtained from the individual stripe-shaped light detection elements 51 is processed using a spatial filter as in a sensing device, the size and the moving speed of the fine particle can be easily obtained. In this case, however, there is a certain tradeoff between the particle size and the moving speed.

This method can reduce an amount of data to be processed, compared with a case wherein an image sensor in the form of a matrix is used, and therefore this method is advantageous in that data processing can be performed more easily and rapidly.

Figure 6:
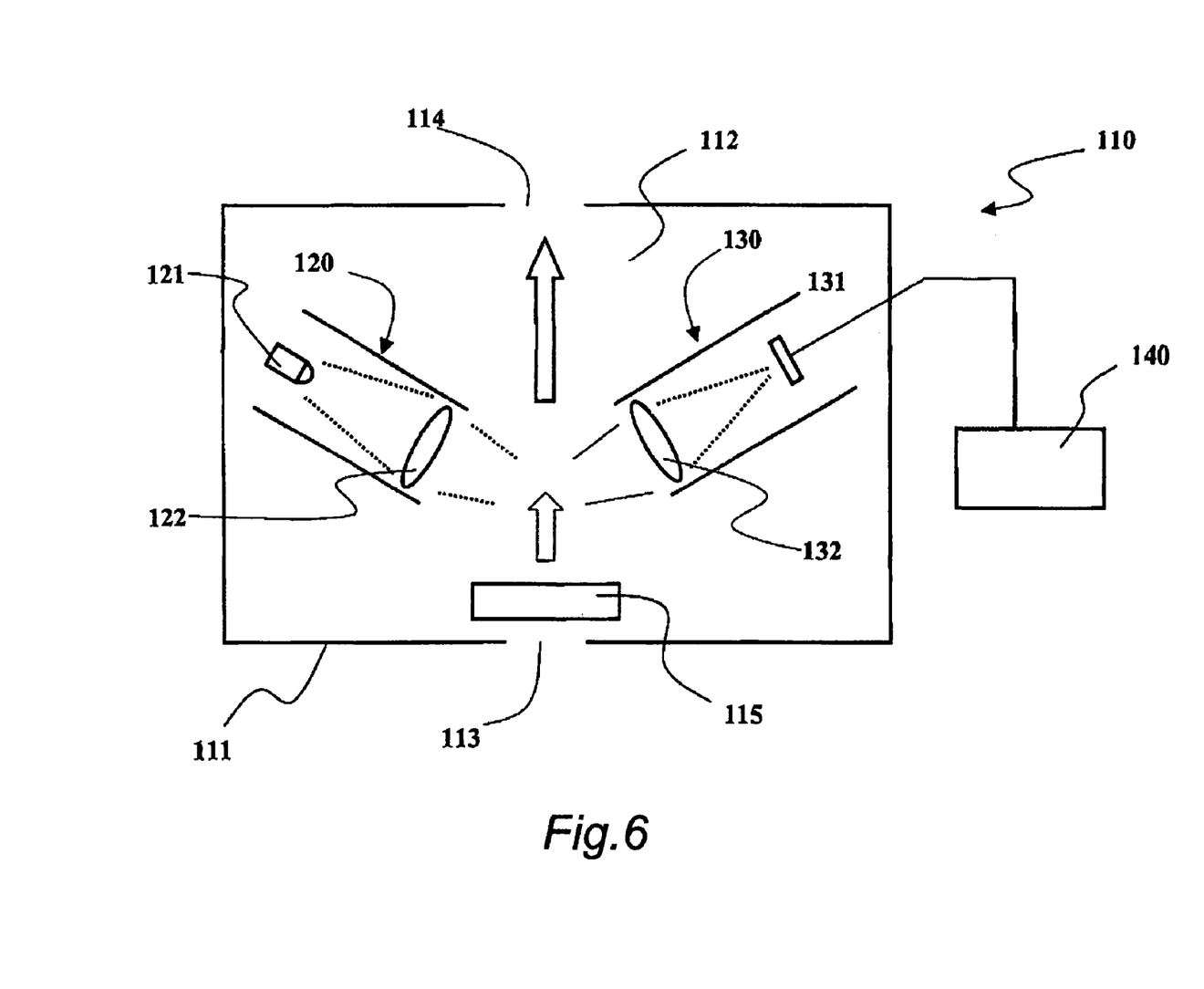
FIG. 6 is a schematic view showing a configuration of a particle detection apparatus according to a second embodiment of the present invention.

FIG. 6 is a schematic view showing the configuration of a particle detection apparatus according to a second embodiment of the present invention. In the first embodiment, a particle detection apparatus utilizing transmitted light was described. However, with a method of measuring reflected light or scattered light as described in FIG. 6, it is possible to detect smoke particles, dust and pollen. The description of operation of each component is omitted by attaching thereto a reference numeral which is greater by 100 than the numeral reference of a corresponding component shown in FIG. 1.

Regarding the positional relation between a light source 120 and a detection device 130, they are disposed on opposite sides of an airflow, but they are not necessarily disposed in such a way. For example, the light source and the detection device may be disposed on the same side of the airflow, and in that case, light from the light source may be illuminated from either an upstream side or a downstream side of the airflow. Further, the light source and the detection device are disposed in a plane that is orthogonal to the airflow, and they may be disposed not linearly like that of FIG. 1, but in a tilted direction within the plane.

In the apparatus according to the first embodiment, as transmission light is always incident, it has to keep a certain level of an input range. As a result, measurements may not always be performed properly. In contrast, in accordance with the detection system of the second embodiment, a dynamic range of the image sensor of the apparatus can be utilized to advantage. Therefore, it is advantageously suitable for a high sensitive measurement of fine particles.

In the foregoing, the best mode for the particle detection apparatus and the detection method thereof according to the present invention has been described in detail. However, these are just examples and do not limit the present invention. The present invention may be modified or altered in various ways by a person skilled in the art.

For example, in order to prevent fine particles to be detected from adhering to the optical system, wiping means that operates mechanically or by an additional airflow may be provided at a proper position.

Further, the particle detection apparatus may be modified such that the apparatus itself does not have airflow generation/control means, and an airflow is generated manually by a user. For example, an airflow may be generated by vibrating the main body of the apparatus. In this case, in order to reduce an influence of disturbance to photodetection, it is necessary to provide an optical filter that matches a wavelength of emitted light at a prior stage to an image sensor, so as to shorten the focal length of a lens.

This apparatus is applicable to systems that detect fine particles including dust, pollen and smoke particles, such as an air cleaner, an air conditioner, a vacuum cleaner, an air fan, a fire alarm, a sensor for environmental measurement and a fine particle detection apparatus in a clean room.

The invention claimed is:

1. A particle detection apparatus, comprising:
a light source and a photodetector for detecting light from the light source for detecting particles floating in the air at a position through which the light passes; and
an airflow generation/control device capable of controlling an airflow of the air present at the position through which the light passes, so as to keep the airflow at a constant rate;
wherein the photodetector is comprised of an image sensor that is adapted to identify predefined particles from image information including the speed, size and shape of a moving object detected by the image sensor.

2. The particle detection apparatus according to claim 1, wherein the light source and the image sensor are disposed directly across from and facing one another so that the light from the light source is directly received by the image sensor, and the airflow generated by the airflow generation/control device flows between the light source and the image sensor.

3. The particle detection apparatus according to claim 1, wherein the light source and the image sensor are disposed across from one another and at an angle to one another so that the image sensor indirectly receives scattered light or reflected light produced within the airflow from the light of the light source.

4. The particle detection apparatus according to claim 1, wherein a relative weight of the moving object is measured from the speed of the moving object.

5. The particle detection apparatus according to claim 4, wherein the light source comprises a semiconductor light-emitting element.

6. The apparatus of claim 1, wherein the constant rate of the airflow is nearly zero.

7. A particle detection method comprising the steps of:
  generating an airflow in the air in which particles are floating;
  illuminating light to a position where the airflow is generated;
  detecting the light passing through the airflow or light scattered by the particles in the airflow; and
  identifying predefined particles from image information including the speed, size and shape of a moving object determined from the detected light and generating an output signal based on identification of the predetermined particles.

8. The particle detection method according to claim 7, further comprising the step of measuring a relative weight of the moving object from the speed of the moving object.

9. The particle detection method according to claim 7, wherein said light is provided by a semiconductor light-emitting element.

10. The method of claim 7, wherein the airflow has a rate of nearly zero.

* * * * *